(12) United States Patent
Fargo

(10) Patent No.: US 9,862,572 B2
(45) Date of Patent: Jan. 9, 2018

(54) SYSTEM AND METHOD FOR MONITORING WIRE ROPES

(71) Applicant: Otis Elevator Company, Farmington, CT (US)

(72) Inventor: Richard N. Fargo, Plainville, CT (US)

(73) Assignee: Otis Elevator Company, Farmington, CT (US)

(*) Notice: Subject to any disclaimer, the term of this patent is extended or adjusted under 35 U.S.C. 154(b) by 112 days.

(21) Appl. No.: 14/775,867

(22) PCT Filed: Mar. 15, 2013

(86) PCT No.: PCT/US2013/032272
§ 371 (c)(1),
(2) Date: Sep. 14, 2015

(87) PCT Pub. No.: WO2014/142998
PCT Pub. Date: Sep. 18, 2014

(65) Prior Publication Data
US 2016/0023865 A1 Jan. 28, 2016

(51) Int. Cl.
*B66B 7/12* (2006.01)
*G01N 27/04* (2006.01)
*G01N 27/20* (2006.01)

(52) U.S. Cl.
CPC .............. *B66B 7/1223* (2013.01); *B66B 7/12* (2013.01); *B66B 7/1207* (2013.01); *G01N 27/041* (2013.01); *G01N 27/20* (2013.01)

(58) Field of Classification Search
CPC .... B66B 7/1207; B66B 7/1223; G01N 27/20; G01N 27/041
See application file for complete search history.

(56) References Cited

U.S. PATENT DOCUMENTS 4,145,920 A * 3/1979 Yamagami ............ B66B 7/1223
187/266
4,434,873 A * 3/1984 Ohta ..................... B66B 7/1223
187/277

(Continued)

FOREIGN PATENT DOCUMENTS

CN 101152943 4/2008
CN 101456509 6/2009

(Continued)

OTHER PUBLICATIONS

EP search report for EP13878179.4 dated Oct. 20, 2016.
Chinese office action for CN201380074718.9 dated Oct. 8, 2016.
Office action for EP13878179.4 dated Oct. 16, 2017.

*Primary Examiner* — Jeff Natalini
(74) *Attorney, Agent, or Firm* — O'Shea Getz P.C.

(57) ABSTRACT

A system and method for monitoring a first wire rope and a second wire rope is provided. The first and second wire ropes each include a contact portion that contacts a sheave, a first end portion, and a monitored portion that extends between the contact portion and the first end portion. The sheave electrically connects the contact portions of the first and second wire ropes. The system includes a controller that is electrically connected to each of the first and second wire ropes to form a circuit with the monitored portions of the first and second wire ropes. The controller selectively applies a signal to the monitored portions of the first and second wire ropes and determines an electrical characteristic thereof. The controller uses the determined electrical characteristic to determine a condition of the first and second wire ropes.

21 Claims, 8 Drawing Sheets

(56) References Cited

U.S. PATENT DOCUMENTS

| | | | |
|---|---|---|---|
| 5,307,672 | A | 5/1994 | Macchiarulo et al. |
| 6,653,943 | B2 | 11/2003 | Lamb et al. |
| 6,986,409 | B2 | 1/2006 | Birbaumer |
| 7,123,030 | B2 | 10/2006 | Robar et al. |
| 7,653,506 | B2 | 1/2010 | Stucky et al. |
| 7,801,690 | B2 | 9/2010 | Veronesi et al. |
| 8,011,479 | B2 | 9/2011 | Stucky et al. |
| 2003/0062225 | A1* | 4/2003 | Stucky .................. B66B 7/123 187/393 |
| 2003/0121729 | A1 | 7/2003 | Guenther et al. |
| 2005/0063449 | A1 | 3/2005 | Lustenberger |
| 2007/0008103 | A1* | 1/2007 | Nicolls .............. G01R 31/3277 340/515 |
| 2007/0056804 | A1 | 3/2007 | Thielow |
| 2008/0223668 | A1* | 9/2008 | Stucky ................. B66B 7/1223 187/393 |
| 2011/0148442 | A1 | 6/2011 | Berner et al. |
| 2011/0253487 | A1 | 10/2011 | Kocher et al. |
| 2011/0284331 | A1 | 11/2011 | Stucky et al. |
| 2012/0021858 | A1 | 1/2012 | Matsuda et al. |
| 2014/0182975 | A1* | 7/2014 | Ikonen ................. B66B 5/0031 187/251 |

FOREIGN PATENT DOCUMENTS

| | | |
|---|---|---|
| DE | 3934654 | 5/1991 |
| JP | H06345351 | 12/1994 |
| JP | 08119123 | 5/1996 |
| JP | 2002348068 | 12/2002 |
| JP | 200499186 | 4/2004 |

\* cited by examiner

SYSTEM AND METHOD FOR MONITORING WIRE ROPES

This application claims priority to PCT Patent Appln. No. PCT/US13/32272 filed Mar. 15, 2013.

BACKGROUND

1. Technical Field

Aspects of the present invention relate to systems and methods for monitoring wire ropes, and more particularly relates to systems and methods for monitoring wire ropes that aid in hoisting an object, and contact an electrically connecting sheave.

2. Background Information

Hoisting systems (e.g., elevator systems, crane systems) often include a rope or a belt that aid in hoisting an object (e.g., an elevator car) and a counterweight. A sheave that is driven by a machine may move the rope or belt to cause movement of the hoisted object and the counterweight. Traditionally, wire ropes were used. More recently, belts have been used. One example of a belt is a coated steel belt having a plurality of steel cords encased in a polyurethane jacket. There is a need to monitor the rope or belt over time; e.g., to determine if the rope or belt is experiencing wear or other damage that may cause weakening. Aspects of the present invention involve systems and methods for monitoring wire ropes.

SUMMARY

According to an aspect of the present invention, a system for monitoring a first wire rope and a second wire rope is provided. The first and second wire ropes each include a contact portion that contacts a sheave, a first end portion, and a monitored portion that extends between the contact portion and the first end portion. The sheave electrically connects the contact portions of the first and second wire ropes. The system includes a controller that is electrically connected to each of the first and second wire ropes to form a circuit with the monitored portions of the first and second wire ropes. The controller selectively applies a signal to the monitored portions of the first and second wire ropes and determines an electrical characteristic thereof. The controller uses the determined electrical characteristic to determine a condition of the first and second wire ropes.

According to another aspect of the present invention, a method for monitoring a first wire rope and a second wire rope is provided. The first and second wire ropes each include a contact portion that contacts a sheave, a first end portion, and a monitored portion that extends between the contact portion and the first end portion. The sheave electrically connects the contact portions of the first and second wire ropes. The method includes the steps of: (1) providing a system that includes a controller that is electrically connected to each of the first and second wire ropes to form a circuit with the monitored portions of the first and second wire ropes; (2) using the controller to selectively apply a signal to the monitored portions of the first and second wire ropes and to determine an electrical characteristic thereof; and (3) using the controller to determine a condition of the first and second wire ropes based on the determined electrical characteristic of the monitored portions of the first and second wire ropes.

These and other aspects of the present invention will become apparent in light of the drawings and detailed description provided below.

DETAILED DESCRIPTION

Figure 1:
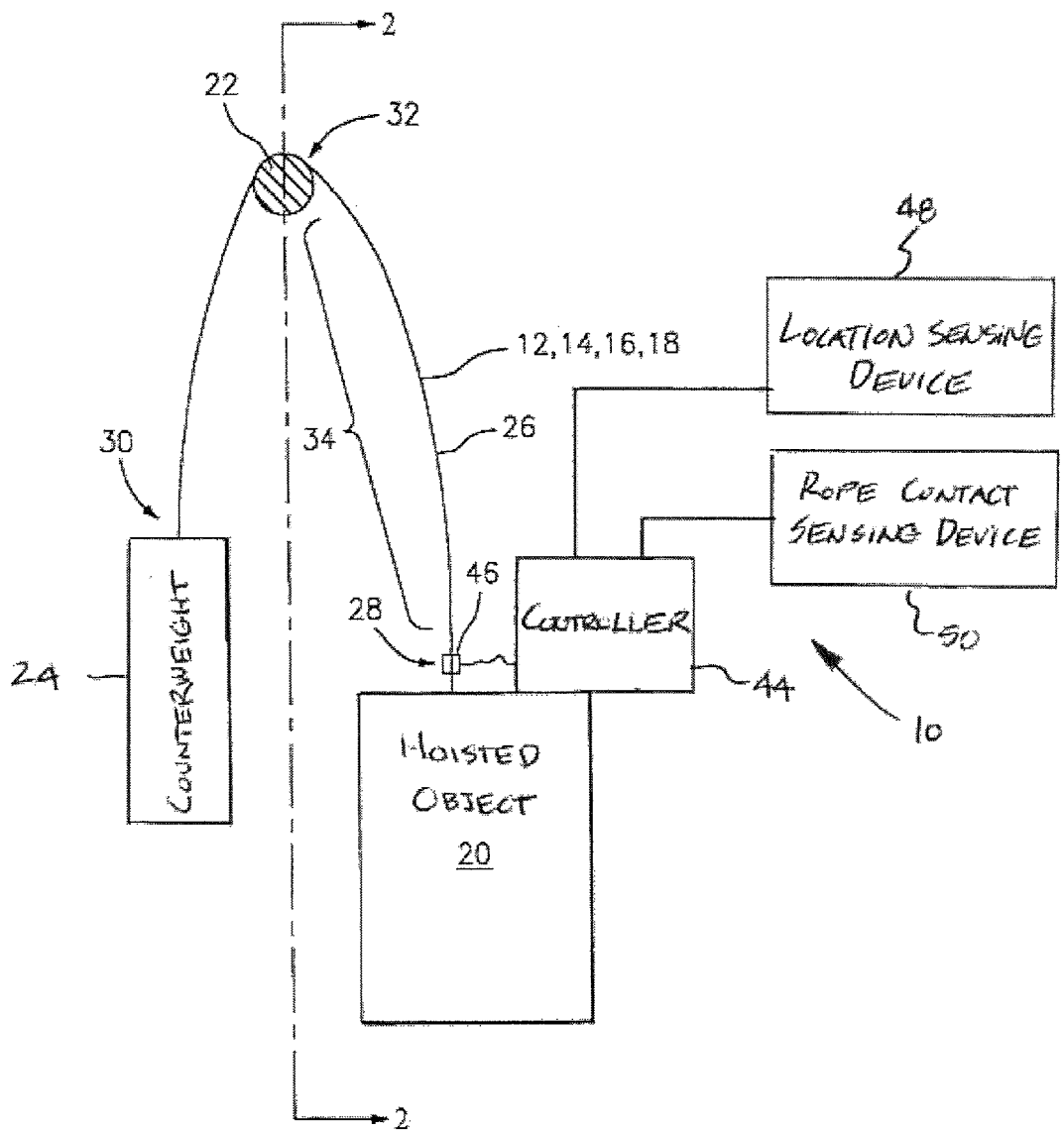
FIG. 1 schematically illustrates an embodiment of the system.
Figure 2:
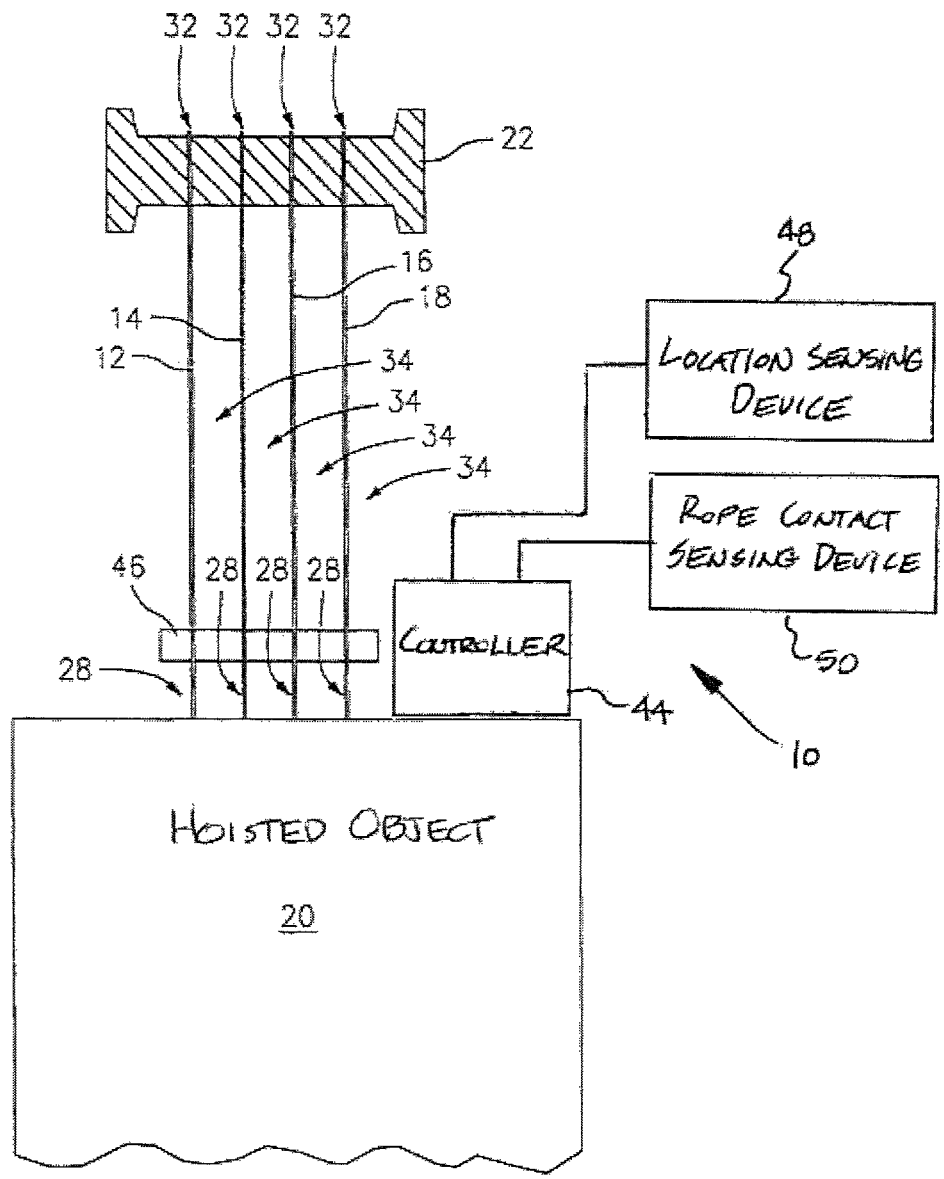
FIG. 2 schematically illustrates another view of the system of FIG. 1.
Figure 3:
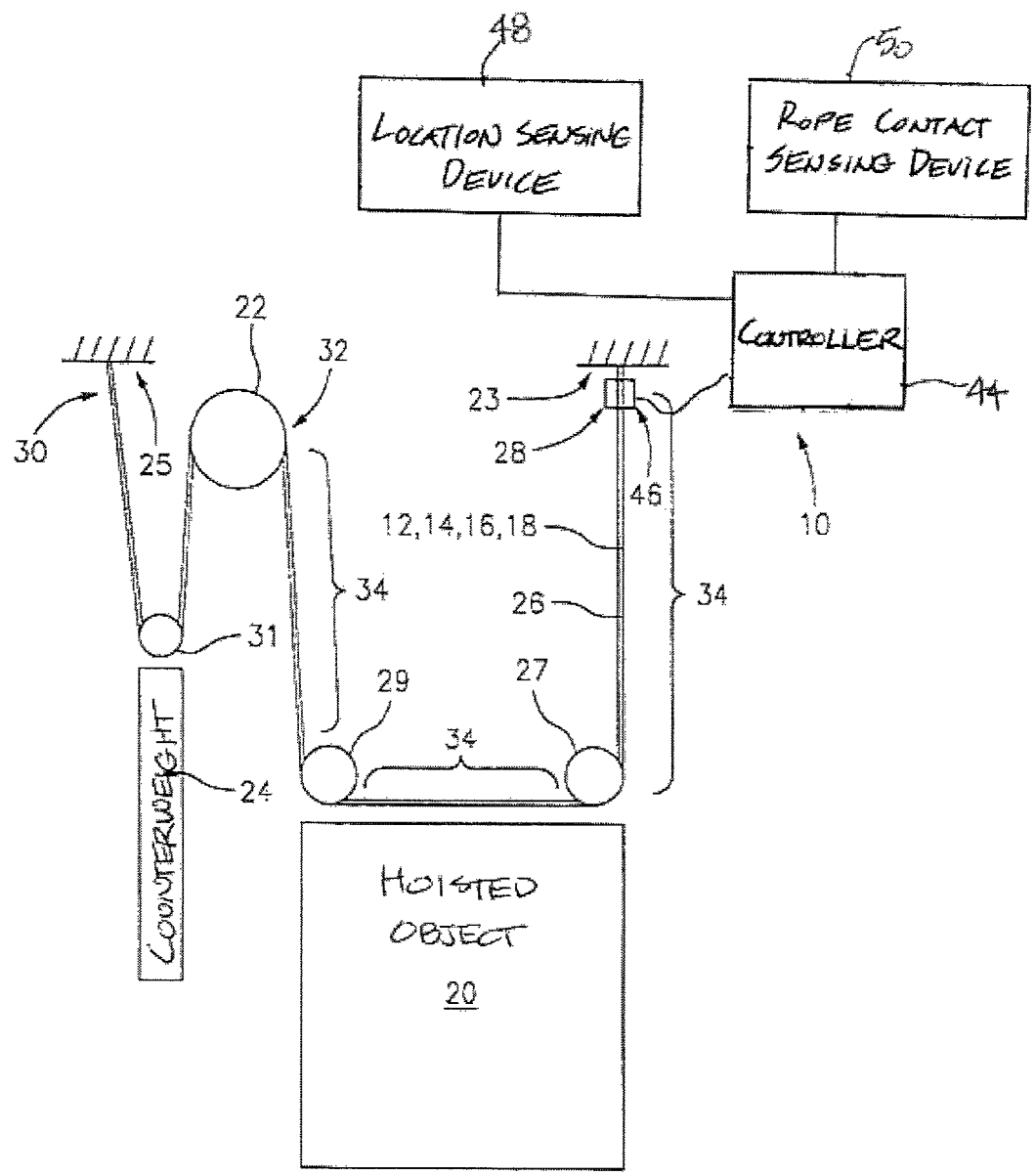
FIG. 3 schematically illustrates another embodiment the system.

Referring to FIGS. 1-3, the present disclosure describes embodiments of a system 10 for monitoring a condition of a plurality of wire ropes 12, 14, 16, 18. The wire ropes 12, 14, 16, 18 aid in hoisting an object 20, and they contact an electrically connecting sheave 22. Aspects of the present invention are not limited to the embodiment shown in FIGS. 1-3. In the embodiment illustrated in FIGS. 1 and 2, the system 10 is used to monitor four (4) wire ropes 12, 14, 16, 18 in a 1:1 roping configuration. In FIGS. 1 and 2, the wire ropes 12, 14, 16, 18 extend between a hoisted object 20 and a counterweight 24 and contact an electrically connecting sheave 22. In the embodiment illustrated in FIG. 3, the system 10 is used to monitor four (4) wire ropes 12, 14, 16, 18 in a 2:1 roping configuration. In FIG. 3, the wire ropes 12, 14, 16, 18 extend between first and second hoistway ceiling mounts 23, 25, and contact an electrically connecting sheave 22, as well as several electrically non-connecting sheaves 27, 29, 31. In FIG. 3, first and second electrically non-connecting sheaves 27, 29 are connected to a hoisted object 20, and a third electrically non-connecting sheave 31 is connected to a counterweight 24. In other embodiments, the system 10 may be used to monitor greater than or less than four (4) wire ropes 12, 14, 16, 18 and/or the system 10 may be used to monitor wire ropes 12, 14, 16, 18 that are arranged in another roping configuration.

The wire ropes 12, 14, 16, 18 each include a plurality of electrically conductive wire strands that are wound together in a known manner to form the wire ropes 12, 14, 16, 18. The wire strands may be made of steel, or another acceptable material. Referring to FIGS. 1 and 3, the wire ropes 12, 14, 16, 18 each include a body 26 that extends between first and second end portions 28, 30 of the wire rope 12, 14, 16, 18. In the embodiment illustrated in FIGS. 1 and 2, the first end portions 28 of the wire ropes 12, 14, 16, 18 are connected to the hoisted object 20, and the second end portions 30 of the wire ropes 12, 14, 16, 18 are connected to the counterweight 24. In the embodiment illustrated in FIG. 3, the first end portions 28 of the wire ropes 12, 14, 16, 18 are connected to the first hoistway ceiling mount 23, and the second end portions 30 of the wire ropes 12, 14, 16, 18 are connected to the second hoistway ceiling mount 25. The body 26 of each wire rope 12, 14, 16, 18 is electrically uninsulated; e.g., along the body 26, the wire strands of the wire rope 12, 14, 16, 18 may be exposed. The first and second end portions 28, 30 of each wire rope 12, 14, 16, 18 are electrically insulated; e.g., the first and second end portions 28, 30 may be encased in a polyurethane jacket. The body 26 of each wire rope 12, 14, 16, 18 includes a contact portion 32 that is in contact with the electrically connecting sheave 22. The position of the contact portions 32 on the wire ropes 12, 14, 16, 18 changes as the wire ropes 12, 14, 16, 18 are moved relative to the electrically connecting sheave 22. The wire ropes 12, 14, 16, 18 each include a monitored portion 34 that extends between the first end portion 28 and the contact portion 32. The portion of the wire rope 12, 14, 16, 18 that is the monitored portion 34 changes as the wire ropes 12, 14, 16, 18 are moved relative to the electrically connecting sheave 22. As will be described in detail below, the system 10 monitors an electrical characteristic of the monitored portions 34 of the wire ropes 12, 14, 16, 18.

Figure 4:
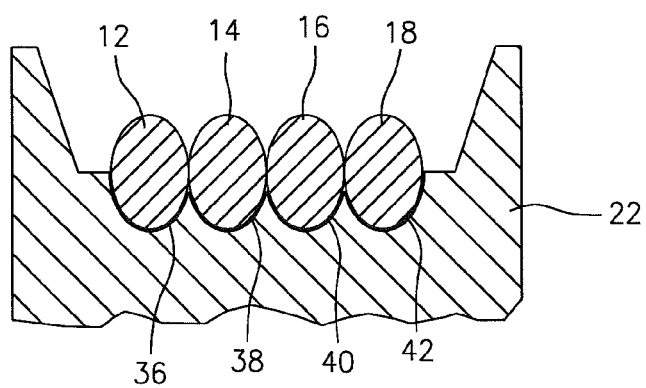
FIG. 4 illustrates a partial sectional view of an electrically connecting sheave with wire ropes contacting it.

The electrically connecting sheave 22 electrically connects the contact portions 32 of the wire ropes 12, 14, 16, 18 to one another. In some embodiments, including the embodiments illustrated in FIGS. 1-3, the electrically connecting sheave 22 is electrically conductive, and thus the contact portions 32 of the wire ropes 12, 14, 16, 18 are electrically connected to one another because they are in contact with the electrically connecting sheave 22. In other embodiments, the electrically connecting sheave 22 may not be electrically conductive, but the electrically connecting sheave 22 may cause the contact portions 32 of the wire ropes 12, 14, 16, 18 to physically touch one another, thereby electrically connecting them. In FIG. 4, for example, the electrically connecting sheave 22 includes a plurality of grooves 36, 38, 40, 42 that receive the contact portions 32 of the wire ropes 12, 14, 16, 18. The grooves 36, 38, 40, 42 are configured so that, when the contact portions 32 of the wire ropes 12, 14, 16, 18 sit within the respective grooves 36, 38, 40, 42, the contact portions 32 of adjacent wire ropes 12, 14, 16, 18 physically touch one another.

In embodiments that include electrically non-connecting sheaves 27, 29, 31, the electrically non-connecting sheaves 27, 29, 31 do not electrically connect the wire ropes 12, 14, 16, 18 to one another. In some embodiments, the electrically non-connecting sheaves 27, 29, 31 may be electrically non-conductive. In some embodiments, the electrically non-connecting sheaves 27, 29, 31 physically separates the wire ropes 12, 14, 16, 18 from one another when they contact the electrically non-connecting sheaves 27, 29, 31.

The hoisted object 20 can be any object capable of being hoisted. In the embodiments illustrated in FIGS. 1-3, the hoisted object 20 is an elevator car.

The system 10 includes a controller 44. In some embodiments, the system 10 may additionally include a connector 46, a location sensing device 48, and/or a rope contact sensing device 50.

The controller 44 is selectively electrically connected, directly or indirectly, to the first end portions 28 of at least two (2) of the wire ropes 12, 14, 16, 18 to form a circuit with the monitored portions 34 of the respective wire ropes 12, 14, 16, 18. The controller 44 is operable to selectively apply a signal to the monitored portions 34 of the respective wire ropes 12, 14, 16, 18 and determine an electrical characteristic (e.g., an electrical resistance) thereof. For example, the controller 44 may selectively apply a signal having a known electrical current to the monitored portions 34 of the respective wire ropes 12, 14, 16, 18, and may determine the electrical resistance thereof by measuring a voltage across the monitored portions 34 of the respective wire ropes 12, 14, 16, 18 by applying Ohm's law. The controller 44 uses the determined electrical characteristic to determine a condition of the respective wire ropes 12, 14, 16, 18; e.g., to determine whether the respective wire ropes 12, 14, 16, 18 are experiencing wear or other damage that may cause weakening. The controller 44 is adapted (e.g., programmed) to selectively perform the functions described herein. The functionality of the controller 44 may be implemented using hardware, software, firmware, or a combination thereof. In embodiments in which the controller 44 determines an electrical resistance of the monitored portions 34 of the wire ropes 12, 14, 16, 18, for example, the controller 44 may include an electrical current source and a volt meter. A person skilled in the art would be able to adapt (e.g., program) the controller 44 to perform the functionality described herein without undue experimentation.

Figure 5:
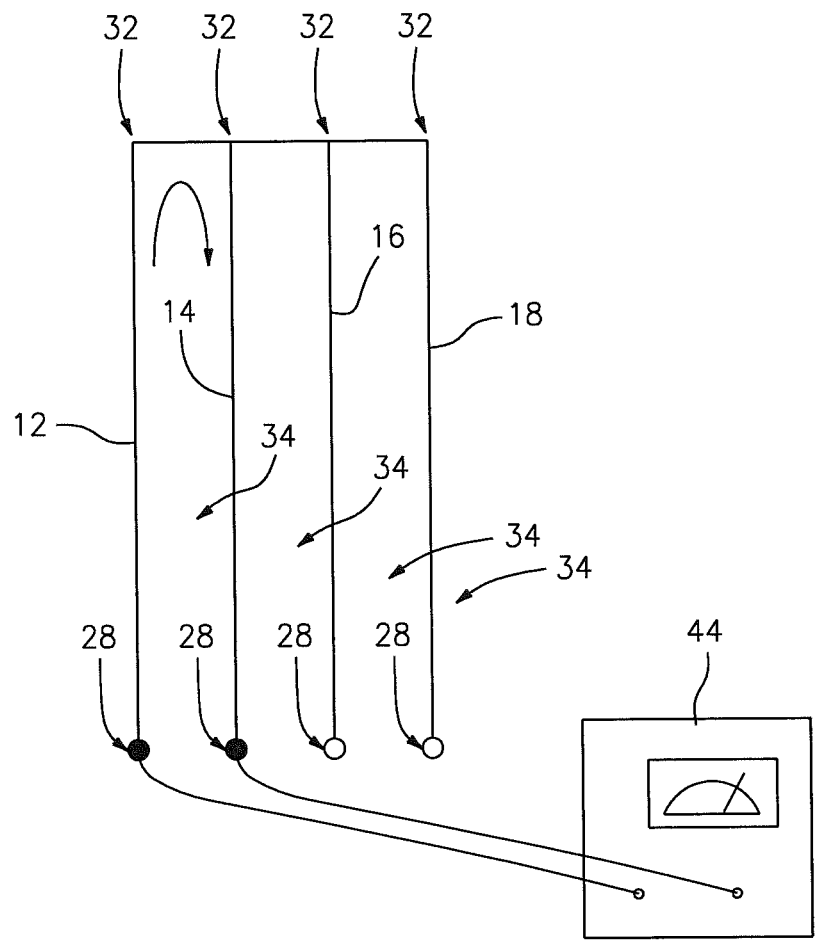
FIG. 5 schematically illustrates an electrical connection configuration of the system of FIG. 1.

In the electrical connection configuration illustrated in FIG. 5, a circuit is formed by electrical connection of the controller 44 to the first end portion 28 of the first wire rope 12 and the first end portion 28 of the second wire rope 14, and by electrical connection of the contact portions 32 of the first and second wire ropes 12, 14 by the electrically connecting sheave 22. The controller 44 is not electrically connected to the first end portions 28 of the third and fourth wire ropes 16, 18, and as a result, the monitored portions 34 of the third and fourth wire ropes 16, 18 do not form part of the circuit. The controller 44 is operable to selectively apply a signal to the monitored portions 34 of the first and second wire ropes 12, 14 and determine the electrical resistance thereof.

Figure 6:
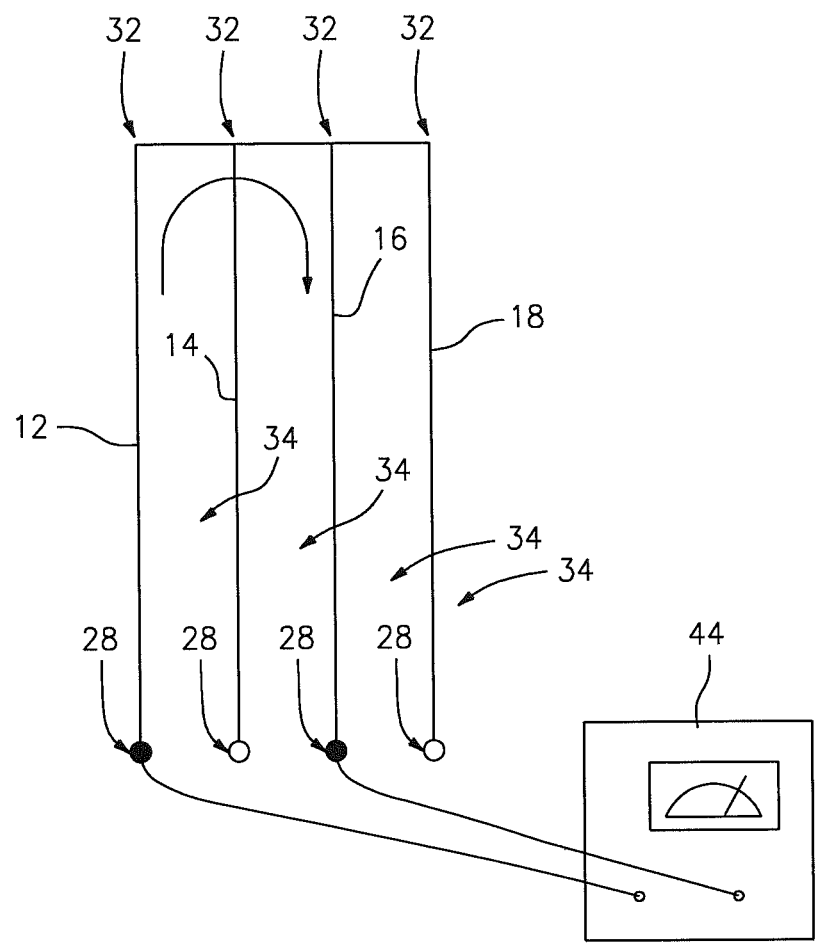
FIG. 6 schematically illustrates another electrical connection configuration of the system of FIG. 1.

In the electrical connection configuration illustrated in FIG. 6, a circuit is formed by electrical connection of the controller 44 to the first end portion 28 of the first wire rope 12 and the first end portion 28 of the third wire rope 16, and by electrical connection of the contact portions 32 of the first and third wire ropes 12, 16 by the electrically connecting sheave 22. The controller 44 is not electrically connected to the first end portions 28 of the second and fourth wire ropes 14, 18, and as a result, the monitored portions 34 of the second and fourth wire ropes 14, 18 do not form part of the circuit. The controller 44 is operable to selectively apply a signal to the monitored portions 34 of the first and third wire ropes 12, 16 and determine the electrical resistance thereof.

Figure 7:
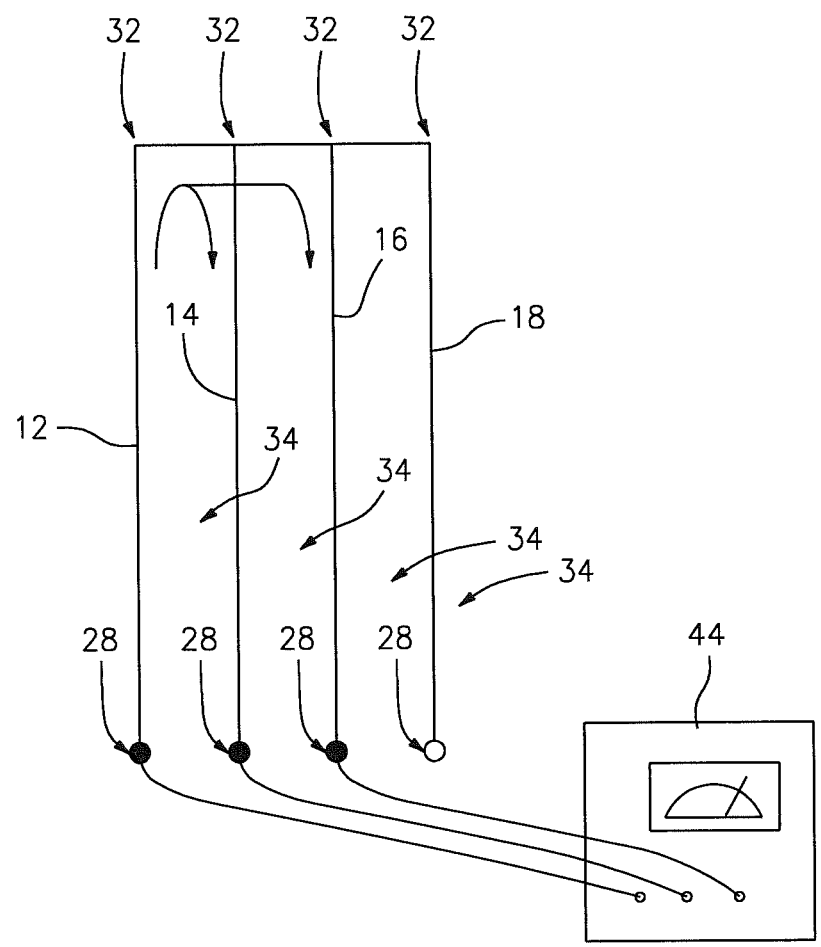
FIG. 7 schematically illustrates another electrical connection configuration of the system of FIG. 1.

In the electrical connection configuration illustrated in FIG. 7, a circuit is formed by electrical connection of the controller 44 to the first end portion 28 of the first wire rope 12, the first end portion 28 of the second wire rope 14, and the first end portion 28 of the third wire rope 16, and by electrical connection of the contact portions 32 of the first, second, and third wire ropes 12, 14, 16 by the electrically connecting sheave 22. The controller 44 is not electrically connected to the first end portion 28 of the fourth wire rope 18, and as a result, the monitored portions 34 of the fourth wire rope 18 does not form part of the circuit. The controller 44 is operable to selectively apply a signal to the monitored portions 34 of the first, second, and third wire ropes 12, 14, 16 and determine the electrical resistance thereof.

Although the electrical connection configurations illustrated in FIGS. 5-7 show a single electrical connection between the controller 44 and each of the first end portions 28 of the respective wire ropes 12, 14, 16, 18, in some embodiments there may be more than one electrical connection between each of the first end portions 28 of the respective wire ropes 12, 14, 16, 18. For example, the controller 44 may selectively apply a signal to the monitored portions 34 of the respective wire ropes 12, 14, 16, 18 using a first electrical connection, and may measure a voltage across the monitored portions 34 of the respective wire ropes 12, 14, 16, 18 using a second electrical connection. The use of more than one electrical connection between the controller 44 and the first end portions 28 of the respective wire ropes 12, 14, 16, 18 may aid in reducing errors associated with contact resistance between the controller 44 and the wire ropes 12, 14, 16, 18. Such errors may arise, for example, because the wire ropes 12, 14, 16, 18 typically have an electrical resistance that is relatively low in magnitude.

In some embodiments, including the embodiment in FIGS. 1-3, the system 10 additionally includes a connector 46 that independently and selectively controls the electrical connection between the controller 44 and each of the first end portions 28 of the wire ropes 12, 14, 16, 18. The functionality of the connector 46 may be implemented using hardware, software, firmware, or a combination thereof. In some embodiments, the connector 46 may independently and selectively control the physical connection between the controller 44 and each of the first end portions 28 of the wire ropes 12, 14, 16, 18. In such embodiments, the connector 46 may include a plurality of electrically conductive lead wires (not shown) and one or more actuators (not shown). The actuators may be operable to independently and selectively actuate (e.g., in response to a signal from the controller 44) each of the lead wires between a connected position and an unconnected position. In the connected position, each lead wire may physically touch one or more of the wire ropes 12, 14, 16, 18, and/or another component that is electrically connected to the wire ropes 12, 14, 16, 18 (e.g., an electrically conductive termination structure that connects the wire ropes 12, 14, 16, 18 to the hoisted object 20). By physically touching the one or more wire ropes 12, 14, 16, 18, and/or another component that is electrically connected to the wire ropes 12, 14, 16, 18, each lead wire may electrically connect the controller 44 to the respective wire ropes 12, 14, 16, 18. In the unconnected position, each lead wire may be physically separated from the respective wire ropes 12, 14, 16, 18 and any other component that is electrically connected to the respective wire ropes 12, 14, 16, 18, and thus the controller 44 may be electrically unconnected from the respective wire ropes 12, 14, 16, 18. In other embodiments, the connector 46 may include a plurality of electrically conductive lead wires (not shown) that are permanently physically touching, and thus permanently electrically connected to, the first end portions 28 of the wire ropes 12, 14, 16, 18 and/or another component that is electrically connected to the wire ropes 12, 14, 16, 18. In such embodiments, the connector 46 also includes one or more switches (not shown) that may be disposed electrically between the controller 44 and the lead wires of the connector 46. In some embodiments, the switches may be mechanical switches that are independently and selectively switchable (e.g., by a known actuator, in response to a signal from the controller 44) between a connected positioned and an unconnected position. In other embodiments, the switches may be electrical switches (e.g., implemented using transistors) that are independently and selectively switchable (e.g., in response to a signal from the controller 44) between a connected positioned and an unconnected position. In the connected position, the switches electrically connect the controller 44 to the respective lead wires, which in turn electrically connect the controller 44 to the respective wire ropes 12, 14, 16, 18 that the respective lead wires are permanently physically touching. In the unconnected position, the switches do not electrically connect the controller 44 to the respective lead wires, and thus the controller 44 is not electrically connected to the respective wire ropes 12, 14, 16, 18 that the respective lead wires are permanently physically touching. A person skilled in the art would be able to adapt (e.g., program) the connector 46 to perform the functionality described herein without undue experimentation. Although the connector 46 is described herein as being separate from the controller 44, in some embodiments the connector 46 may be implemented as a feature of the controller 44.

In embodiments in which there are more than two (2) wire ropes 12, 14, 16, 18, the connector 46 enables the system 10 to selectively switch between different electrical connection configurations. For example, the controller 44 may enable the system 10 to selectively switch between the electrical connection configurations shown in FIGS. 5-7, or other electrical connection configurations. The connector 46 may therefore enable the system 10 to selectively monitor different groups or combinations of the wire ropes 12, 14, 16, 18. In embodiments in which there are more than two (2) wire ropes 12, 14, 16, 18, the connector 46 may enable the system 10 to determine an electrical characteristic of the monitored portion 34 of one (1) of the wire ropes 12, 14, 16, 18. In the embodiment illustrated in FIGS. 1 and 2, for example, the connector 46 may enable the system 10 to switch between three electrical connection configurations: (1) a first electrical connection configuration (see FIG. 5) that enables a first measurement (M1) equal to the sum of the electrical resistance of the first wire rope 12 (R1) and the electrical resistance of the second wire rope 14 (R2); (2) a second electrical connection configuration (see FIG. 6) that enables a second measurement (M2) equal to the sum of the electrical resistance of the first wire rope 12 (R1) and the electrical resistance of the third wire rope 16 (R3); and (3) a third electrical connection configuration (not shown) that enables a third measurement (M3) equal to the sum of the electrical resistance of the second wire rope 14 (R2) and the electrical resistance of the third wire rope 16 (R3). The electrical resistance of the second wire rope 14 (R2) can be determined by the controller 44 using the following equation: $R2=(M1+M3-M2)/2$.

In some embodiments, including the embodiments illustrated in FIGS. 1-3, the system 10 additionally includes a location sensing device 48 that generates a location signal indicative of a length of the monitored portions 34 of the wire ropes 12, 14, 16, 18; e.g., indicative of a location of the hoisted object 20 relative to the electrically connecting sheave 22. The location sensing device 48 is adapted (e.g., programmed) to selectively perform the functions described herein. The functionality of the location sensing device 48 may be implemented using hardware, software, firmware, or a combination thereof. In some embodiments, for example, the location sensing device 48 may include a rotational sensor connected to the electrically connecting sheave 22 for measuring its rotational position, and a plurality of discrete location sensors positioned in the hoistway within which the system 10 is operated. In such embodiments, the location sensing device 48 may be able to account for stretching and/or creeping of the wire ropes 12, 14, 16, 18, which might otherwise cause errors when determining a location of the hoisted object 20 relative to the electrically connecting sheave 22. A person skilled in the art would be able to adapt (e.g., program) the location sensing device 48 to perform the functionality described herein without undue experimentation. Although the location sensing device 48 is described herein as being separate from the controller 44, in some embodiments the location sensing device 48 may be implemented as a feature of the controller 44.

Figure 8:
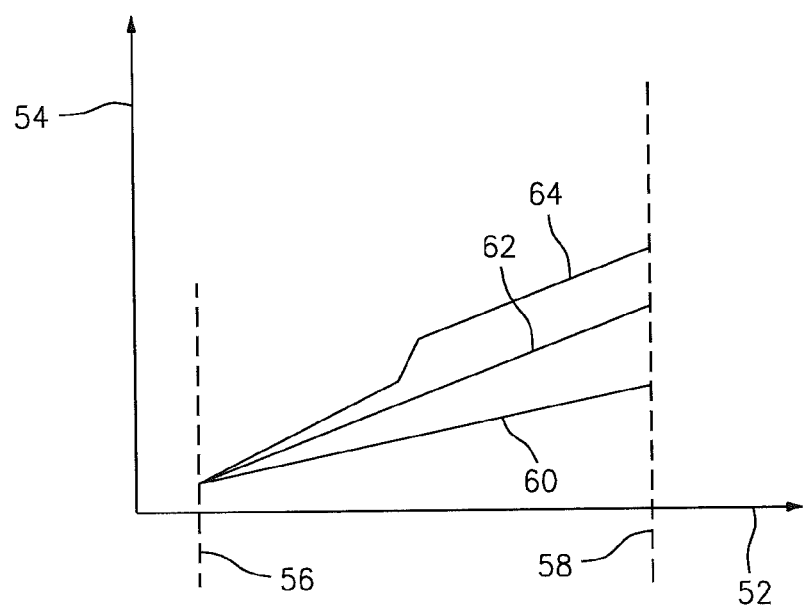
FIG. 8 is a plot of data generated by the controller included in the system of FIG. 1.

In embodiments in which the system 10 includes a location sensing device 48, the controller 44 may receive the location signal from the location sensing device 48, and may use the location signal alone or together with the determined electrical characteristic of the monitored portions 34 of the respective wire ropes 12, 14, 16, 18 to determine a condition of the respective wire ropes 12, 14, 16, 18. In some embodiments, the controller 44 may use the location signal to determine how the electrical characteristic of the monitored portions 34 of the wire ropes 12, 14, 16, 18 changes as the location of the hoisted object 20 changes. For example, the controller 44 may generate data similar to that plotted in FIG. 8. In FIG. 8, the axis 52 represents a length of the monitored portions 34 of the wire ropes 12, 14, 16, 18, and the axis 54 represents the electrical resistance of the monitored portions 34 of the wire ropes 12, 14, 16, 18. The length 56 represents the shortest possible length of the monitored portions 34 of the wire ropes 12, 14, 16, 18, and the length 58 represents the longest possible length of the monitored portions 34 of the wire ropes 12, 14, 16, 18. The data plotted on the first curve 60 is representative of new wire ropes 12, 14, 16, 18. The data plotted on the second curve 62 is representative of old wire ropes 12, 14, 16, 18 that are experiencing uniform wear. The uniform wear causes the second curve 62 to have an increased slope relative to the first curve 60. The data plotted on the third curve 64 is representative of old wire ropes that are experiencing both uniform wear and localized wear. The localized wear causes the third curve 64 to have a non-linear portion. In some embodiments, the controller 44 may generate data similar to that plotted in FIG. 8, and may analyze such data to determine, for example, whether wire ropes 12, 14, 16, 18 are experiencing uniform wear and/or localized wear.

In some embodiments, the location sensing device 48 may compare the determined electrical characteristic of the monitored portions 34 of the respective wire ropes 12, 14, 16, 18 with an expected value to determine if the location of the hoisted object 20 relative to the electrically connecting sheave 22 is incorrect. The location of the hoisted object 20 relative to the electrically connecting sheave 22 may be incorrect, for example, if the wire ropes 12, 14, 16, 18 have lost traction with the electrically connecting sheave 22, causing them to slip relative to the electrically connecting sheave 22. The location sensing device 48 may determine the expected value, for example, using historical electrical characteristic data and the location signal from the location sensing device 48. Historical electrical characteristic data similar to that plotted in FIG. 7 may be saved, for example, to a memory device included in the location sensing device 48. If the location sensing device 48 determines that the distance between the hoisted object 20 and the electrically connecting sheave 22 is incorrect, the location sensing device 48 may send an alert signal to a machine controller (not shown) that controls the machine (not shown) that drives the electrically connecting sheave 22 and/or an electrically non-connecting sheave 27, 29, 31. In response to the alert signal, the machine controller may cause the machine to stop, or the machine controller may cause the machine to drive the electrically connecting sheave 22 and/or an electrically non-connecting sheave 27, 29, 31 until the distance between the hoisted object 20 and the electrically connecting sheave 22 is correct.

In some embodiments, including the embodiment in FIGS. 1-3, the system 10 additionally includes a rope contact sensing device 50 that compares the determined electrical characteristic of the monitored portions 34 of the respective wire ropes 12, 14, 16, 18 with an expected value to determine if the respective wire ropes 12, 14, 16, 18 are contacting one another along their monitored portions 34. Such contact between the monitored portions 34 of the respective wire ropes 12, 14, 16, 18 may be caused, for example, if the hoisted object 20 sways. Referring to the electrical connection configuration in FIG. 5, for example, if the monitored portions 34 of the first and second wire ropes 12, 14 contact each other, they will form a shorting connection there between, which may result in the determined electrical characteristic being significantly different than an expected value. The rope contact sensing device 50 may determine the expected value, for example, using historical electrical characteristic data and the location signal from the location sensing device 48. Historical electrical characteristic data similar to that plotted in FIG. 8 may be saved, for example, to a memory device included in the rope contact sensing device 50. If the rope contact sensing device 50 determines that the respective wire ropes 12, 14, 16, 18 are contacting one another along their monitored portions 34, it may send an alert signal to a machine controller (not shown) that controls the machine (not shown) that drives the electrically connecting sheave 22 and/or an electrically non-connecting sheave 27, 29, 31. In response to the alert signal, the machine controller may cause the machine to stop, or the machine controller may cause the machine to drive the electrically connecting sheave 22 and/or an electrically non-connecting sheave 27, 29, 31 until the hoisted object 20 is positioned at location where it will not experience sway. The rope contact sensing device 50 is adapted (e.g., programmed) to selectively perform the functions described herein. The functionality of the rope contact sensing device 50 may preferably be implemented using software. In some embodiments, the rope contact sensing device 50 may additionally or alternatively be implemented using hardware, firmware, or a combination thereof. A person skilled in the art would be able to adapt (e.g., program) the rope contact sensing device 50 to perform the functionality described herein without undue experimentation. Although the rope contact sensing device 50 is described herein as being separate from the controller 44, in some embodiments the rope contact sensing device 50 may be implemented as a feature of the controller 44.

While several embodiments have been disclosed, it will be apparent to those of ordinary skill in the art that aspects of the present invention include many more embodiments and implementations. Accordingly, aspects of the present invention are not to be restricted except in light of the attached claims and their equivalents.

What is claimed is:

1. A system for monitoring a first wire rope and a second wire rope, the first and second wire ropes each including a contact portion that contacts a sheave, a first end portion, and a monitored portion that extends between the contact portion and the first end portion, the sheave electrically connecting the contact portions of the first and second wire ropes, the system comprising:
   a controller that is electrically connected to each of the first and second wire ropes to form a circuit with the monitored portions of the first and second wire ropes;
   wherein the controller selectively applies a signal to the monitored portions of the first and second wire ropes and determines an electrical characteristic thereof;
   wherein the controller uses the determined electrical characteristic to determine a condition of the first and second wire ropes.

2. The system of claim 1, wherein the first and second wire ropes each include a plurality of electrically conductive wire strands that are wound together.

3. The system of claim 1, wherein the first wire rope includes a body that extends between the first end portion of the first wire rope and a second end portion of the first wire rope, and wherein the second wire rope includes a body that extends between the first end portion of the second wire rope and a second end portion of the second wire rope.

4. The system of claim 3, wherein the body of the first wire rope is electrically uninsulated, and wherein the body of the second wire rope is electrically uninsulated.

5. The system of claim 4, wherein the body of the first wire rope includes the contact portion of the first wire rope, and wherein the body of the second wire rope includes the contact portion of the second wire rope.

6. The system of claim 1, wherein the sheave is electrically conductive.

7. The system of claim 1, wherein the sheave is configured so that the contact portions of the first and second wire ropes physically touch one another.

8. The system of claim 1, wherein the determined electrical characteristic is an electrical resistance.

9. The system of claim 1, further including a connector that independently and selectively controls the electrical connection between the controller and each of the first and second wire ropes.

10. The system of claim 1, further including a location sensing device that generates a location signal indicative of a length of the monitored portions of the first and second wire ropes.

11. The system of claim 10, wherein the controller receives the location signal from the location sensing device and uses the location signal together with the determined electrical characteristic to determine the condition of the first and second wire ropes.

12. The system of claim 11, wherein the first and second wire ropes aid in hoisting an object, wherein the location sensing device compares the determined electrical characteristic of the monitored portions of the first and second wire ropes with an expected value to determine if a location of the hoisted object relative to the electrically connecting sheave is incorrect, and wherein the location signal is further indicative of the location.

13. The system of claim 11, further including a rope contact detector that compares the determined electrical characteristic with an expected value to determine if the monitored portions of the first and second wire ropes are contacting one another.

14. The system of claim 13, wherein the expected value is determined using historical electrical characteristic data and the location signal.

15. The system of claim 1, wherein the first wire rope and the second wire rope each comprise an electrically uninsulated body that contacts the sheave.

16. A method for monitoring a first wire rope and a second wire rope, the first and second wire ropes each including a contact portion that contacts a sheave, a first end portion, and a monitored portion that extends between the contact portion and the first end portion, the sheave electrically connecting the contact portions of the first and second wire ropes, the method comprising:

providing a system that includes a controller that is electrically connected to each of the first and second wire ropes to form a circuit with the monitored portions of the first and second wire ropes; and using the controller to selectively apply a signal to the monitored portions of the first and second wire ropes and to determine an electrical characteristic thereof;

using the controller to determine a condition of the first and second wire ropes based on the determined electrical characteristic of the monitored portions of the first and second wire ropes.

17. The method of claim 16, wherein the system further includes a location sensing device that generates a location signal indicative of a length of the monitored portions of the first and second wire ropes, and wherein the method further comprises:

using the controller to receive the location signal from the location sensing device and to determine the condition of the first and second wire ropes based on the location signal and the determined electrical characteristic of the monitored portions of the first and second wire ropes.

18. The method of claim 17, wherein the first and second wire ropes aid in hoisting an object, and wherein the method further comprises:

using the location sensing device to compare the determined electrical characteristic of the monitored portions of the first and second wire ropes with an expected value to determine if a location of the hoisted object relative to the electrically connecting sheave is incorrect;

wherein the location signal is further indicative of the location.

19. The method of claim 16, wherein the system further includes a rope contact sensing device, and wherein the method further comprising:

using the rope contact sensing device to compare the determined electrical characteristic of the monitored portions of the first and second wire ropes with an expected value to determine if the monitored portions of the first and second wire ropes are contacting one another.

20. The method of claim 16, wherein an electrically conductive body of the first wire rope contacts and thereby is electrically connected to an electrically conductive body of the second wire rope at the sheave.

21. The method of claim 16, wherein an electrically conductive body of the first wire rope contacts and thereby is electrically connected to the sheave, an electrically conductive body of the second wire rope contacts and thereby is electrically connected to the sheave, and the sheave electrically connects the electrically conductive body of the first wire rope to the electrically conductive body of the second wire rope.

* * * * *